United States Patent [19]

Durrwachter et al.

[11] Patent Number: 5,124,489
[45] Date of Patent: Jun. 23, 1992

[54] PROCESS FOR PREPARING PHENETHANOL ETHERS BY THE REDUCTION OF CORRESPONDING PHENYLGLYOXAL ACETALS

[75] Inventors: John R. Durrwachter, Corpus Christi, Tex.; Michael Meier, Frankfurt, Fed. Rep. of Germany; Graham N. Mott; Werner H. Mueller, both of Corpus Christi, Tex.

[73] Assignee: Hoechst Celanese Corporation, Somerville, N.J.

[21] Appl. No.: 755,913

[22] Filed: Sep. 6, 1991

Related U.S. Application Data

[63] Continuation-in-part of Ser. No. 628,238, Dec. 13, 1990, which is a continuation-in-part of Ser. No. 451,675, Dec. 14, 1989, abandoned.

[51] Int. Cl.$^5$ .............................................. C07C 41/28
[52] U.S. Cl. ...................................... 568/630; 562/478
[58] Field of Search ......................... 568/630; 562/478

[56] References Cited

FOREIGN PATENT DOCUMENTS 885030 12/1980 Belgium .
2432563 2/1975 Fed. Rep. of Germany .
3539629 5/1987 Fed. Rep. of Germany .
2487338 1/1982 France .

OTHER PUBLICATIONS

March, Jerry; "Advanced Organic Chemistry" (1985) John Wiley & Sons New York, pp. 393-394 (3rd Ed.).
Larock, Richard; "Comprehensive Organic Transformations" (1989) pp. 35-36.
Sandler, Stanley et al.; "Organic Functional Group Preparations" (1972) Academic Press, New York (vol. III) p. 68.
Noller, Carl "Chemistry of Organic Compounds" (1965) W. B. Saunder Co. Philadelphia, p. 243 and 844.
2 Pharmaceutical Manufacturing Encyclopedia, 1009-1010 (2nd ed. 1988).
Hallberg, et al., a New Route to 4-(2'-Methoxyethyl)-Phenol via Palladium-catalyzed Arylation of Methyl Vinyl Ether, 15(13) *Synthetic Com.*, 1131-6 (1985).
Baird et al., Neighboring Carbon and Hydrogen, L. I. Dienones from AR, Θ-3 Participation. Isolation and Behavior of Spiro(2,5)octa-1,4-diene-3-one, 85 *Am. Chem. Soc.* 567-575 (1962).
Communication to the Editor from Baird et al, 79 *Am. Chem. Soc.* 756-757 (1957).

*Primary Examiner*—Marianne M. Cintins
*Assistant Examiner*—John D. Peabody, III
*Attorney, Agent, or Firm*—D. R. Cassady; A. Triantaphyllis; J. M. Mazzarese

[57] ABSTRACT

Substituted phenethanol ethers are prepared by the catalytic reduction of corresponding substituted phenylglyoxal acetals. The catalytic reduction is carried out by reacting a substituted phenylglyoxal acetal with hydrogen in the presence of an acid catalyst and a metal catalyst. Certain substituted phenylglyoxal acetals, and more particularly, 4-hydroxyphenylglyoxal dialkyl acetals are prepared by reacting 4-hydroxyacetophenone with a primary or a secondary alkyl alcohol in the presence of a hydrogen ion (H+) source and a nitrosonium ion (NO+) source.

12 Claims, No Drawings

PROCESS FOR PREPARING PHENETHANOL ETHERS BY THE REDUCTION OF CORRESPONDING PHENYLGLYOXAL ACETALS

RELATED APPLICATIONS

This application is a continuation-in-part application of co pending U.S. application Ser. No. 07/628,238 filed on Dec. 13, 1990, which is a continuation-in-part of application Ser. No. 07/451,675, now abandoned.

TECHNICAL FIELD OF THE INVENTION

The present invention relates to substituted phenethanol ethers and, more particularly, to a process for the preparation thereof. Still more particularly, the present invention discloses a process for preparing substituted phenethanol ethers by the catalytic reduction of corresponding substituted phenylglyoxal acetals. Furthermore, the present invention relates to a process for the preparation of certain phenylglyoxal acetals. Furthermore, the present invention discloses certain novel phenylglyoxal acetal and phenethanol ether compounds.

BACKGROUND OF THE INVENTION

The compound 4-(2'-methoxyethyl)phenol, a substituted phenethanol ether prepared in accordance with the present invention, is a known compound. It is used as an intermediate in the production of 1-[4-(2-methoxyethyl)phenoxy]-3-[1-(1-methoxyethyl)amino]-2-propanol, a beta-adrenergic blocker known as metroprolol tartrate and described in 2 Pharmaceutical Manufacturing Encyclopedia, 1009-1010 (2nd ed. 1988.).

Several methods have been employed in the past to manufacture 4-(2'-methoxyethyl)phenol. A method is described in Baird et.al., Neighboring Carbon and Hydrogen. LI[1] Dienones from Ar, Θ-3 Participation. Isolation and Behavior of Spiro (b 2,5; ocra-I,4-diene-3-one, 85 Am. Chem. Soc'y 567, 575 (1963) and in Communication to the Editor from Baird, et.al., 79 Am. Chem. Soc'y 756-757 (1957). In that method, 4-(2,-methoxyethyl)phenol is synthesized from phenylacetic acid through a multi-step process.

French Patent 2,487,338 discloses the preparation of 4-(2,-methoxyethyl)phenol utilizing brominated alkoxyphenol as a starting material. The method utilizes a multi-step process which includes a technically difficult Grignard reaction.

Belgian patent 885,030 discloses another method for the preparation of 4-(2'-methoxyethyl)phenol. In that method, the starting material is 4-hydroxystyrene. Several steps are used to obtain the final product.

Still another method for the production of 4-(2'-methoxyethyl)phenol is disclosed in Hallberg, et.al., A New Route to 4-(2-Methoxyethyl)phenol via Palladium-catalyzed Arylation of Methyl Vinyl Ether, 15(13) Synthetic Com., 1131-6 (1985; wherein 4-(2'-methoxyethyl)phenol is prepared via palladium-catalyzed arylation of methyl vinyl ether. The palladium catalyzed reaction of methyl vinyl ether with 4-bromonitrobenzene, followed by hydrogenation and subsequent diazotization forms 4-(2'-methoxyethyl)phenol.

One of the disadvantages of the above referenced processes is that they include several, often complex, steps which give rise to economical and ecological problems. Furthermore, another disadvantage of some of the above referenced processes was that they utilize expensive starting material.

According to the present invention, a simple economical method is disclosed wherein 4-hydroxyphenylglyoxal dimethyl acetal is catalytically reduced to prepare 4-(2'-methoxyethyl)phenol. The method is also employed to prepare other substituted phenethanol ethers which are believed to be useful as intermediates in pharmaceutical products by the catalytic reduction of corresponding substituted phenylglyoxal acetals. Furthermore, according to the present invention, a simple economical process is described for the preparation of certain such acetals and, more particularly, 4-hydroxyphenylglyoxal dialkyl acetals from 4-hydroxyacetophenone. Co pending U.S. Pat. application Ser. No. 07/628,238, filed on Dec. 13, 1990, discloses the preparation of certain hydroxyaromatic ketoacetals from hydroxyaromatic methylketones. The entire content of that application is incorporated herein and is part hereof by reference.

German patent 2,432,563 discloses the oxidation of substituted acetophenones using alkyl nitrites in alcohol/hydrochloric acid to prepare substituted phenylglyoxalacetals. Furthermore, German Patent No. 3,539,629 discloses a method of oxidizing substituted acetophenones using dinitrogentrioxide in alcohol/hydrochloric acid to prepare appropriate substituted phenylglyoxal acetals.

These and other advantages and objects of the present invention will become apparent from the following description.

SUMMARY OF THE INVENTION

Substituted phenethanol ethers are produced by catalytically reducing corresponding substituted phenylglyoxal acetals. According to the invention, a phenylglyoxal acetal reacts with hydrogen in the presence of an acid catalyst and a metal catalyst to prepare the corresponding phenethanol ether. The method is used for the production of a variety of substituted phenethanol ethers including, but not limited to, 4-(2'-methoxyethyl)phenol, 4- (2'-isopropoxyethyl)phenol, and 4-[2'-(3''-methylbutoxy)ethyl]phenol. The acid catalyst is a strong acid such as hydrochloric acid or phosphoric acid. A metal catalyst is a metal selected from the Group VIII metals of the periodic table of the elements such as Pd, Pt or Ni.

The reaction is preferably carried out in the presence of a solvent in an enclosed reactor with the pressure of the reactor being provided by hydrogen under pressure being in the range of about 15 psig to about 1000 psig and at a temperature in the range of about $-20°$ C. to about $150°$ C. for about 0.5 to about four (4) hours. Upon completion of the reaction, the reaction mass may be treated by well known separation techniques to recover the product, the acid and metal catalyst and the solvent.

Certain phenylglyoxal acetals and, more particularly, hydroxyaromatic ketoacetals which may be used for the preparation of corresponding phenethanol ethers by the method described above are prepared from hydroxyaromatic methylketones. According to that method, 4-hydroxyacetophenone is reacted with a primary or a secondary alkyl alcohol in the presence of a source of a hydrogen ion (H+) and a source of a nitrosonium ion (NO+). The source of the hydrogen ion is a strong mineral acid such as hydrochloric acid or sulfuric acid. The method is used for the preparation of several hydroxyaromatic ketoacetals including, but not limited, 4-hydroxyphenylglyoxal dimethyl acetal, 4-hydroxyphenylglyoxal diisopropyl acetal and 4-hydroxyphenylglyoxal diisoamyl acetal.

The source of the nitrosonium ion can be an alkyl nitrite used in combination with an acid source such as sulfuric acid, a hydrochloric acid. Alternatively, the source of the nitrosonium ion can be a NO+X- reactant wherein X is a halogen, a sulfite, a sulfate, phosphite or a phosphate.

The reaction for converting a hydroxyaromatic methyl ketone to a hydroxyaromatic ketoacetal is carried out at a temperature in the range of about −20° C. to about 50° C. for a time period of about one (1) to about twenty-four (24) hours. The 4-hydroxyphenylglyoxal dialkyl acetals prepared by this method can be used for the preparation of corresponding phenethanol ethers, as described above. Accordingly, the two methods may be combined to prepare phenethanol ethers from 4-hydroxyacetophenone in a two-step process.

Novel compounds are disclosed which are prepared by the above processes. Those compounds are 4-hydroxyphenylglyoxal dimethyl acetal, 4-hydroxyphenylglyoxal diisopropyl acetal, 4-hydroxyphenylglyoxal diisoamyl acetal, 4-(2'-isopropoxyethyl)phenol, and 4-[2'-(3''-methylbutoxy)ethyl]phenol.

DETAILED DESCRIPTION OF THE INVENTION (a) Preparation of Phenethanol Ethers from Phenylglyoxal Acetals According to the present invention, a substituted phenethanol ether is prepared by the catalytic reduction of a corresponding substituted phenylglyoxal acetal and, more particularly, by the hydrogenation of such acetal in the presence of a suitable acid catalyst and a suitable metal catalyst. The substituted phenethanol ethers prepared in accordance with the present invention are of the formula

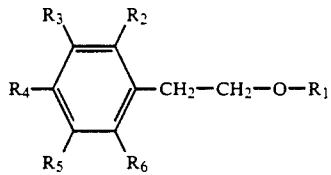

which is hereinafter referred to as Formula 1. The corresponding reactant substituted phenylglyoxal acetal is of the formula

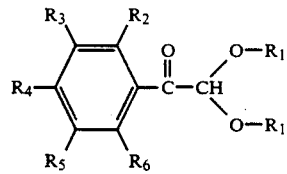

which is hereinafter referred to as Formula 2.

In Formulas 1 and 2, $R_1$ is a primary or a secondary alkyl group containing, preferably one (1) to twenty (20) carbon atoms and, most preferably, one (1) to six (6) carbon atoms. Furthermore, in Formulas 1 and 2, $R_2$, $R_3$, $R_4$, $R_5$ and $R_6$, are independently hydrogen, an alkyl group, a substituted or an unsubstituted aryl group, a hydroxy group, an alkoxy group, a substituted or an unsubstituted aryloxy group, a halogen, a carboxylic acid group, a carboxylic acid derivative group, an acyloxy group, an aroyloxy group, an amino group, an alkyl substituted amino group, a substituted or an unsubstituted aryl substituted amino group or an amino group. When $R_2$, $R_3$, $R_4$, $R_5$ or $R_6$ is an alkyl group, said group contains, preferably one (1) to twenty (20) carbon atoms and, most preferably, one (1) to six (6) carbon atoms. When $R_2$, $R_3$, $R_4$, $R_5$ and $R_6$ is a substituted or unsubstituted aryl group, said group is preferably a phenyl group. It should be understood that, unless stated otherwise, the above definitions of $R_1$, $R_2$, $R_3$, $R_4$, $R_5$ and $R_6$ shall be applicable hereinafter.

In accordance with the present invention, the catalytic reduction reaction to prepare the phenethanol ethers of Formula 1 from the corresponding phenylglyoxal acetal of Formula 2 is represented stoichiometrically as follows (Reaction 1):

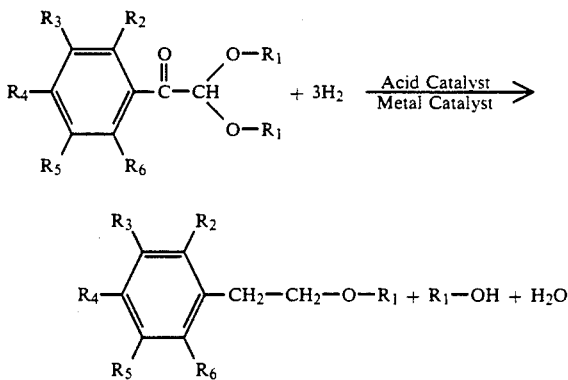

Examples of substituted phenthanol ethers prepared in accordance with the present reaction include, but are not limited to, 4-(2'-methoxyethyl)phenol (Compound III) which is prepared from 4-hydroxyphenylgloxal dimethyl acetal (Compound IV); 4-(2'-isopropoxyethyl)phenol (Compound V) which is prepared from 4-hydroxyphenylglyoxal diisopropyl acetal (Compound VI); and 4-[2'-(3''-methylbutoxy)ethyl]phenol (Compound VII) which is prepared from 4-hydroxyphenylglyoxal diisoamyl acetal (Compound VIII). These compounds are shown below:

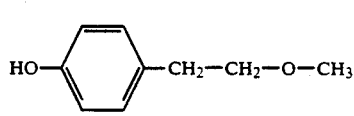
(Compound III)

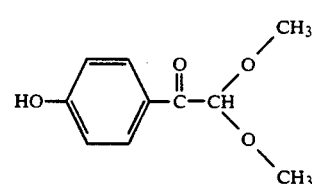
(Compound IV)

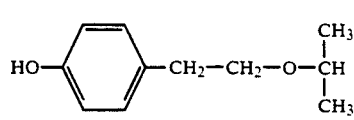
(Compound V)

-continued

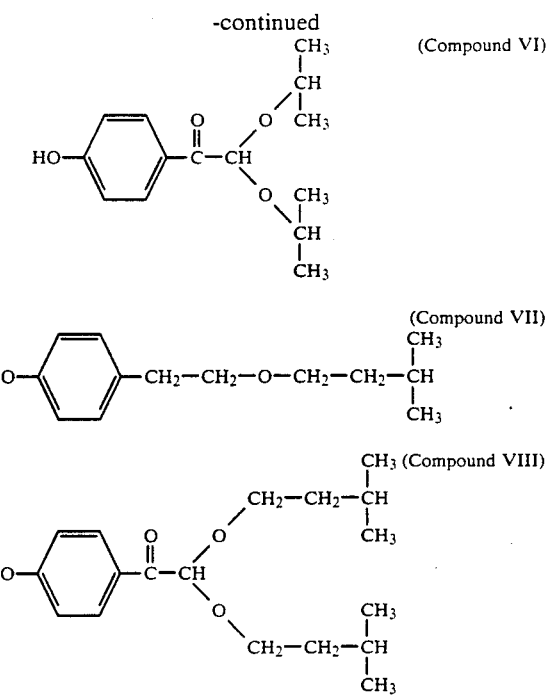

(Compound VI)

(Compound VII)

HO—⟨benzene⟩—CH$_2$—CH$_2$—O—CH$_2$—CH$_2$—CH(CH$_3$)$_2$ (Compound VIII)

It is believed that the metal catalyst promotes the conversion of the

group of the reactant to a

group (Group I), the acid catalyst promotes the hydrogenolysis of the —OH group from said Group I and the hydrogenolysis of one —I—R$_1$ group. Hydrogenolysis refers to the reductive cleavage of a single chemical bond, wherein a hydrogen atom is added to each fragment resulting from said cleavage. It is unexpected that such selective hydrogenolysis is achieved. Accordingly, suitable catalysts that promote these steps are used to carry out the reaction.

The metal catalyst may be any well known hydrogenation catalyst selected from the Group VIII metals such as Pd, Ni or Pt. The preferred catalyst is Pd. The amount of metal catalyst depends on the type used. In the case of Pd supported by carbon (Pd/C), a suitable amount of catalyst is in the range of about 0.1 to about 20 weight percent and preferably in the range of about 0.5 to about 15 weight percent with respect to phenylglyoxal acetal reactant such as 4-hydroxyphenylglyoxal dimethyl acetal, on a dry catalyst basis. Either dry or moist Pd/C catalyst may be used.

Any acid catalyst known to promote a hydrogenolysis reaction as discussed above may be used. The preferred acid catalysts are sulfuric acid or methane sulfonic acid and the most preferred is hydrochloric acid. Although a small amount of acid catalyst is sufficient to promote Reaction 1 of the present invention, it is preferred that an amount of more than one (1) mole of catalyst per mole of reactant be used to carry out the reaction rapidly.

Although it is not necessary for the reaction, the reaction is preferably carried out in the presence of a solvent. Examples of such solvents include polar solvents such as alcohols, ketones, ethers and esters. The preferred solvents are those having high polarity, namely, alcohols such as isopropanol and methanol. A sufficient amount of solvent is used to dissolve the reactant and to maintain the reaction mass in solution.

In carrying out the reaction, the reactant dissolved in the solvent, the acid catalyst and the metal catalyst are charged to a corrosion-resistant reactor. The reactor is purged with an inert gas as nitrogen.

Although a stoichiometric amount of hydrogen is sufficient to carry out the reaction, an excess amount of hydrogen gas under pressure is injected into the reactor. Accordingly, a sufficient amount of hydrogen gas is injected therein to build the partial pressure of hydrogen therein in the range of about 15 psig to about 1000 psig and, preferably, in the range of about 20 psig to about 500 psig. The hydrogen may also be injected gradually by sparger or other similar means.

The reaction is carried out at a temperature preferably in the range of about −20° C. to about 150° C. and, most preferably, in the range of about 20° to about 80° C. The rate of the reaction depends on the amount of acid and metal catalyst, the pressure of the hydrogen gas and the reaction temperature. Preferably, the amount of the catalysts used is within the lower portion of the aforesaid ranges with the temperature and the hydrogen pressure being in the upper portion of the aforesaid ranges. High yields, however, are also observed when the amount of catalysts is in the upper portion of the aforesaid ranges and the reaction temperature and the hydrogen pressure are in the lower portion of their respective aforesaid ranges.

The reaction mass is continuously stirred by well known stirring means. The reaction is carried out for a sufficient period of time to obtain a satisfactory conversion of the reactant to the product. Depending on the amount of the catalysts, the reaction temperature and the hydrogen pressure, the time period may be in the range of about 0.50 hours to about twenty-four (24) hours. Preferably, the reaction is carried out for a time period in the range of about one (1) hour to about three (3) hours. The reaction is relatively slow, and can be carried out in a batch mode, a semi-batch mode, or a continuous mode.

Upon the completion of the reaction, the product may be separated from the reaction mass by well known techniques such as distillation and crystallization. For example, the reaction mass may be rotary vacuum distilled to remove the solvent for further use. Then, the remaining reaction mass may be cooled to crystallize the produce which is subsequently removed by filtration.

The metal catalyst can be recovered by filtration of the reaction mass prior to the removal of the solvent therefrom. The acid catalyst may be recovered with the solvent. Both metal and acid catalysts may be reformulated and recirculated to the reactor for further utilization.

The above process may be used along or may be integrated with a process for preparing the phenylglyoxal acetal reaction. Examples of such process are disclosed below.

(b) Preparation of Phenylglyoxal Acetals

Processes for the preparation of some of the phenylglyoxal acetals of Formula 2 are known. Furthermore, processes for the preparation of certain phenylglyoxal acetals and, more particularly, hydroxyaromatic ketoacetals, from hydroxyaromatic methylketones are disclosed in co pending U.S. Pat. application Serial No. 07/628,238, filed on Dec. 13, 1990 which is incorporated herein and is made part hereof in its entirety by reference.

According to the present invention, a method is disclosed for the preparation of certain phenylglyoxal acetals and, more particularly, hydroxyaromatic ketoacetals of the formula

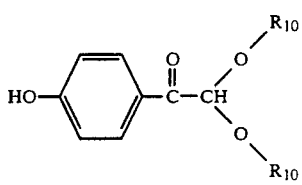

wherein $R_{10}$ is a primary or a secondary alkyl group having typically one to ten carbon atoms. It should be understood that, unless stated otherwise, this definition of $R_{10}$ shall be applicable hereinafter. In said method, 4-hydroxyacetophenone (Compound IX), a compound of the formula

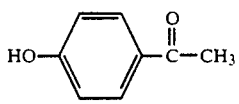

is reacted with a primary or a secondary alkyl alcohol of the formula $R_{10}$—O—H (Formula 4) in the presence of a source of a hydrogen ion (H+) and a source of a nitrosonium ion (NO+). The reaction is represented stoichiometrically as follows.

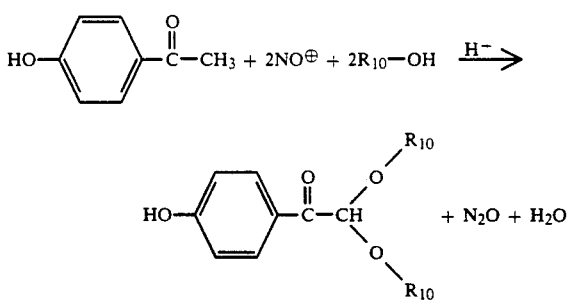

The source of the hydrogen ion (H+) is a strong mineral acid, preferably hydrogen chloride or sulfuric acid. Theoretically, the acid should be present in at least a catalytic amount; preferably, however, it should be present in at least a catalytic amount; preferably, however, it should be present in the composition in an amount of from about one (1) to abut sic (6) mole equivalents of the amount of 4-hydroxyacetophenone, more preferably from about one (1) to about three (3) mole equivalents and most preferably from about one (1) to about two (2) mole equivalents.

The source of the nitrosonium ion (NO+) can be alkyl nitrite of the formula $R_{11}$—O—N═O (Formula 5) used in combination with an acid source such as sulfuric acid, or preferably, hydrogen chloride. $R_{11}$ is an alkyl group having typically one (1) to ten (10) carbon atoms. This definition of $R_{11}$ will be applicable hereinafter, unless stated otherwise. Examples of such nitrites are methyl nitrite, isopropyl nitrite or t-butyl nitrite The alkyl nitrite $R_{11}$—O—N—O and the acid react to form a source of nitrosonium ion. For example, when the acid is hydrogen chloride the alkyl nitrite $R_{11}$—O—N—O reacts with the hydrogen chloride to form $R_{11}$—O—H and NOCl which is the source of the nitrosonium ion (NO+). The alkyl nitrite is preferably present in an amount of from about one (1) to about five (5) mole equivalents of the amount of 4-hydroxyacetophenone, more preferably from about one (1) to about three (3) mole equivalents. When the source of the nitrosonium ion (NO+) is an alkyl nitrite, it is preferred that $R_{10}$ is the same as $R_{11}$.

The source of nitrosonium can also be a reactant NO+X-wherein X is a halogen, a sulfite, a sulfate, a phosphite or a phosphate. X is preferably a halogen and, most preferably, chlorine (Cl).

The primary or secondary alcohol $R_{10}$—O—H is typically methyl alcohol, isopropyl alcohol, sec-butyl alcohol, n-butyl alcohol or isoamyl alcohol. It is preferably present in a large excess of that amount required for the reaction or from about two (2) to about ten (10) times the weight of the 4-hydroxyacetophenone or more preferably from about two (2) to about five (5) times the weight of the 4-hydroxyacetophenone.

It presently appears that the components of the reaction mixture used to form the hydroxyaromatic ketoacetals of Formula 3 in accordance with Reaction 2 may be combined in any order. The reaction mixture is preferably free of water. The reaction is exothermic and requires no heating to drive the reaction. The reaction may be cooled to a convenient working temperature. The reaction is preferably conducted at a temperature of from about −20° C. to about 50° C., or more preferably, from about −10° C. to about 40° C. or, most preferably, from about −10° C. to about 25° C.

Reaction 2 to form the hydroxyaromatic ketoacetal of Formula 3 is conducted for a time period ranging from about one (1) hour. to about 24 hours, more preferably from about one (1) hour to about eight (8) hours, and most preferably form about one (1) hour to about four (4) hours. The reaction can be carried out in a batch mode, a semi-batch mode or a continuous mode.

Without being restricted to a particular theory, it is hypothesized that the reaction proceeds as follows for conversion of 4-hydroxyacetophenone to the hydroxyaromatic ketoacetals of Formula 3. The 4-hydroxyacetophenone (Compound IX) which is initially present in solution, undergoes acid catalyzed tautomerication to the enol form (Compound X) in the presence of a strong mineral acid, preferably HCl. The enol then reacts with a nitrosonium ion (NO+) to form the alpha nitroso-4-hydroxyacetophenone (Compound XI) which undergoes an acid catalyzed tautomerication yielding alpha-oximino-4-hydroxyacetophenone (Compound XII). The nitrosonium ion comes from a NO+ source such as nitrosyl chloride which is generated from the reaction of HCl with alkyl nitrite ($R_{11}$—O—N═O), as described above. Compound XIII then undergoes a solvolysis reaction, aided by a second equivalent of NO+ with the $R_{10}$—OH alcohol solvent forming the hydroxyaromatic ketoacetal of Formula 3.

The above reaction steps are illustrated as follows:

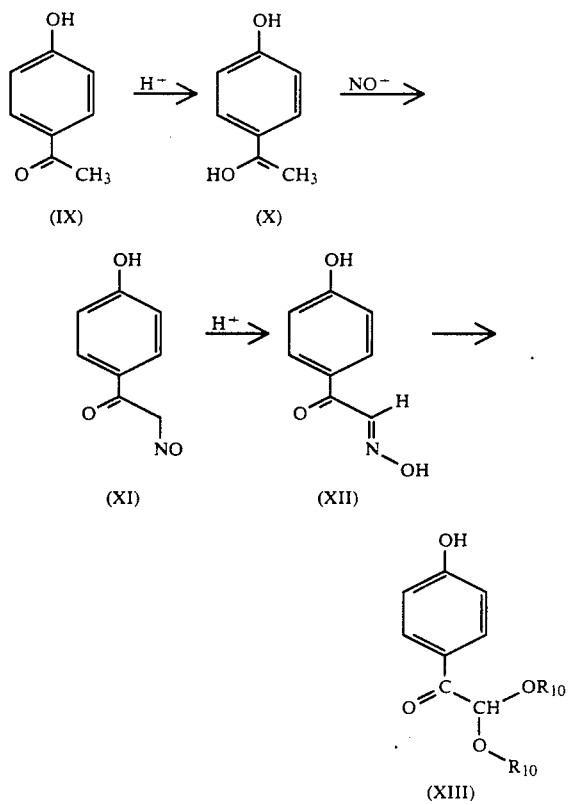

The hydroxyaromatic ketoacetal of Formula 3 which may be otherwise referred to as 4-hydroxyphenylglyoxal dialkyl acetal may be separated from the reaction mass by well knows separation techniques such as distillation, cyrstallization and filtration. For example, the alcohol may be removed by rotary vacuum distillation and the remaining mass may be cooled to crystalize the 4-hydroxyphenylglyoxal dialkyl acetal. Then, the crystallized mass may be filtered and dried to obtain the acetal product.

The above described process for the preparation of 4-hydroxyphenylglyoxal dialkyl acetals may be integrated with the previously described process of preparing corresponding phenethanol ethers. Accordingly, a two-step process may be employed for producing the phenethanol ethers from 4-hydroxyacetophenone.

(c) Preparation of Novel Compounds

The methods described above for the preparation of phenylglyoxal acetals and phenethanol ethers were utilized to prepare novel compounds which are not found in the prior art, namely, 4-hydroxyphenylglyoxal dimethyl acetal (Compound IV); 4-hydroxyphenylglyoxal diisopropyl acetal otherwise referred to as isopropyl acetal of p-hydroxyphenylglyoxal (Compound VI); 4-hydroxyphenylglyoxal diisoamyl acetal otherwise referred to as isoamyl acetal of p-hydroxyphenylglyoxal (Compound VIII); 4-(2'-isopropoxyethyl)phenol otherwise referred to as isopropyl ether of p-hydroxyphenylglyoxal (Compound V); and 4-[2'-(3''-methylbutoxy)ethyl]phenol otherwise referred to as isoamyl ether of p-hydroxyphenethanol (Compound VII). The structural formulas of those compounds are shown above.

The following examples further illustrate the invention but. are not to be construed as limitations on the scope of the invention contemplated herein.

EXAMPLE 1

4-Hydroxyphenylglyoxal Dimethyl Acetal

A methyl nitrite generator was set up by fitting a two-liter, five neck round bottom flask with a thermowell, a 500 mL metering addition funnel, a mechanical stirrer, a nitrogen inlet and a gas outlet attached to Tygon tubing that leads to a fritted gas sparger in the reaction flask described below. The generator was charged with $NaNO_2$ (365g, 5.16 moles), methanol (225 mL) and water (225 mL) to form a slurry mixture. Sulfuric acid (33% aqueous, 568 mL, 6.8 equivalents) was added to the slurry with continuous stirring to generate methyl nitrite.

A reaction flask was set up by fitting a three-liter three-neck round bottom flask with a thermowell, a Friedrich condenser with a gas outlet that led to a vent, and the fritted gas sparger which was connected to the gas outlet from the methyl nitrite generator. The reactor was charged with p-hydroxyacetophenone (272g, 2 moles) and methanolic HCl (600 mL, 1.25 M).

The reactor was initially chilled to about 0° C. with an isopropanol/dry ice bath. During the course of the reaction, the bath was maintained at about −20° C. The generator was not cooled. The rate of addition of the sulfuric acid added to the $NaNO_2$/methanol slurry in the generator to generate methyl nitrite controlled the methyl nitrite evolution. The temperature of the reactor was maintained between 0° and 5° C. by controlling the methyl nitrite rate and the ice bath. The addition of the nitrite from the generator to the reactor was allowed to take place for about four (4) hours.

After the completion of the reaction, the reaction mixture was transferred to a two liter flask with 500 mL of water. The methanol was rapidly removed by rotary vacuum distillation. Upon cooling, the crystalline mass was filtered and dried to yield p-hydroxyphenylglyoxal dimethyl acetal (270g, 83% pure, 57% isolated yield. The filtrate included additional p-hydroxyphenylglyoxal dimethyl acetal for a total yield of about 72%. The product was confirmed by mass spectrometer and nuclear magnetic residence (nmr). [H-nmr (200 MHz, acetone-$d_6$; $\delta$ 3.43 (s, 6H, $CH_3$—O), 5.10 (s, 1 H, C-H), 6.90, 8.0 (dd, 4 H, aromatic), 9.27 (s, 1 H, OH); —C-nmr (50 MHz, acetone-$d_6$); $\delta$ 55.2 ($CH_3$), 105.6 (CH), 127.1, 132.4, 132.9, 163.0 (aromatic), 192.3 (C=O)].

EXAMPLE 2

4-(2'-Methoxyethyl)phenol

A solution of 1.00 g (5.1 mmol) 4-hydroxyphenylglyoxal dimethyl acetal in 10 g methanol containing 0.19 g (5.1 mmol) hydrogen chloride and a 0.05 g moist 10% Pd/C catalyst were loaded into an autoclave. The autoclave was then sealed and purged with nitrogen and pressurized with hydrogen gas to 300 psig. The autoclave was then heated up to 50° C. with stirring at 800 rpm. The reaction was allowed to take place for approximately two (2) hours. The autoclave was then purged with nitrogen and cooled to room temperature. The catalyst was filtered off providing a clear filtrate A 70% yield of 4-(2'-methoxyethyl)phenol was obtained

EXAMPLE 3

4-(2'-Methoxyethyl)phenol

The procedure of Example 2 was repeated with a solution of 2.00 g (10.2 mmol) 4-hydroxyphenylglyoxal dimethyl acetal in 10 g methanol containing 0.23 g (6.3 mmol) hydrogen chloride and 0.20 g moist 10% Pd/C catalyst being reacted with hydrogen ga pressurized at 170 psig at 25° C. with stirring of 550 rpm. A 53% yield of 4-(2'-methoxyethyl)phenol was obtained.

EXAMPLE 4

4-(2'-Methoxyethyl)phenol

The procedure of Example 2 was repeated with a solution of 3.00 g (15.3 mmol) 4-hydroxyphenylglyoxal dimethyl acetal in 10 g methanol containing 0.16 g (4.4 mmol) hydrogen chloride and 0.15 g moist 10% Pd/C catalyst being reacted with hydrogen gas pressurized at 300 psig at 50° C. 300 rpm. A 59% yield of 4-(2'-methoxyethyl)phenol was obtained.

EXAMPLE 5

4-(2'-Methoxyethyl)phenol

The procedure of Example 2 was repeated with a solution of 2.00 g (10.2 mmol) 4-hydroxyphenylglyoxal dimethyl acetal in 10 g methanol containing 0.37 g (10.2 mmol) hydrogen chloride and a 0.20 g dry 10% Pd/C catalyst being reacted with hydrogen gas pressurized at 50 psig at 25° C. A 47% yield of 4-(2'-methoxyethyl)phenol was obtained.

EXAMPLE 6

4-Hydroxyphenylglyoxal Diisoamyl Acetal p-Hydroxyacetophenone (40g, 294 mmol) was charged into a reactor containing acidified isoamyl alcohol (200 mL, acidified with anhydrous HCl). Isoamyl nitrite (79 ml, 69g, 588 mmol) was added slowly to maintain a temperature of 25° C. Reaction was monitored by HPLC. At the end of the reaction, ethyl acetate (500 ml) was added and the reaction mixture was transferred to a separator funnel. The organic layer was washed with water (2 ×250 ml), saturated NaHCO$_3$ (1×250 ml) and brine (1×250 ml). The organic solution was dried over MgSO$_4$ and distilled under reduced pressure to remove solvents. Chromatography over silica gel with CH$_2$Cl$_2$ yielded, after removal of solvent, 56.5 g of product (183 mmol, 62% yield). The product was confirmed by mass spectroscopy and nmr. [$^1$H-nmr(200 MHz, acetone-d$_6$); δ 0.93 (m, 12 H, CH$_3$), 1.4 (m, 4 H, C—CH$_2$—C), 1.7 (m, 2H, —CH—), 3.5 and 3.8 (m, 4 h, —OCH$_2$), 5.1 (s, lH, O—CH—O), 0), 6.9, 8.0 (dd, 2 H each, aromatic), and 9.3 (broad s, 1 H phenolic H); $^{13}$C-nmr (50 MHz, acetone -d$_6$) δ22.7, 22.8 (CH$_3$), 25.6, 39.4 (CH$_2$—CH—), 67.0 (CH$_2$-O), 105.1 (O—CH—O), 115.8, 126.9, 133.1, 163 (aromatic), 192.8 (C=O); MS (direct probe) m/z 308 (M+), 187, 121, 71 (100)].

EXAMPLE 7

4-[2'-(3"-Methylbutoxy)ethyl]phenol

An autoclave was charged with isoamyl acetal of p-hydroxyphenylglyoxal (20 g, 65 mmol), palladium catalyst (2 g, 10% Pd/C 2 mmol) and methanol (150 ml, 5% HCl). After purging with nitrogen, the autoclave was pressured to 50 psig with hydrogen. After three (3) hours, the pressure dropped to 15 psig. The reaction was then recharged with hydrogen to 50 psig for one (1) hour. Then, it was further charged with hydrogen to 200 psig and was allowed to carry out the reaction overnight at 40° C. Analysis indicated a 40% yield of the product 4-2[2'(3"-methylbutoxy)ethyl]phenol, identified by MS m/z 208 (M+), 165, 137.

EXAMPLE 8

4-Hydroxyphenylgloxal Diisopropyl Acetal

Isopropanol (100 ml), p-hydroxyphenylglyoxal (40 g, 294 mmol) and isopropyl nitrite (62 ml, 2 equivalents) were charged into a reaction flask and were stirred to dissolve. The solution was cooled to 0° C. and acidic isopropanol (100 ml, 33% HCl) was added to maintain a temperature of less than 25° C. Additional isopropyl nitrite (25 ml) was added until all starting material and intermediates were undetectable (as determined by HPLC) to complete the reaction. After addition was complete, the reaction mass was allowed to stand overnight. The reaction mass was quenched with water (400 ml) and the oily product formed a separate phase. The product was separated, dissolved in an equal volume of methylene chloride and washed with water and then brine. The solvent was removed under reduced pressure. A sample of this oil (12 g) was recrystallized from 50 ml of 1:1 methyl t-butyl ether:hexane to yield 2 g of purified material. The product was confirmed by mass spectroscopy and nmr. [$^{1/H\text{-}nmr}$(200 MHz, acetone-d$_6$); δ 1.09, 1.22 (d, 12 H, CH$_3$), 3.94 (m, 2 H, O—CH—(CH$_3$)$_2$, 5.14 (s, lH, —CH—(—O-iPr)$_2$), 6.89, 8.10 (dd, 4 H, aromatic), 9.20 (broad s, 1 H, phenolic H); $^{13}$C-nmr (50 MHz, acetone-d$_6$); δ 22.6, 23.4 (CH$_3$), 71.1 (C—O), 103.7 (CH—(O—iPr)$_2$), 115.6, 133.5, 162.8 (aromatic), 193.8 (C=O)].

EXAMPLE 9

Isopropyl Ether of P-Hydroxyphenylglyoxal (4-(2'-Isopropoxyethyl)phenol)

An autoclave was charged with the isopropyl acetal of p-hydroxyphenylglyoxal (6.0 g, 24 mmol), palladium catalyst (2.0 g, 5% Pd on carbon, 1 mmol) and acidic isopropanol (160 ml, 5% HCl). After purging with nitrogen, the reactor was pressured to 200 psig with hydrogen. After four (4) hours, the reactor pressure was only 65 psig. The reactor contents were removed and the catalyst was removed by filtration. Solvent was removed under reduced pressure. The residue was dissolved in ethyl acetate, washed with water and saturated bicarbonate, dried over MgSO. and concentrated (3.4 g, 53% product). The product was confirmed by GC/MS [m/z 180 (M+), 121, 107].

While the invention is described with respect to specific embodiments, modifications thereof can be made by one skilled in the art without departing from the spirit of the invention. The details of said embodiments are not to be construed a limitation except to the extent indicated in the following claim.

We claim:

1. A method of preparing a substituted phenethanol ether, comprising the step of reducing a corresponding substituted phenylglyoxal acetal by reacting said acetal with hydrogen in the presence of an acid catalyst and a metal catalyst.

2. The method according to claim 1 wherein the phenethanol ether is of the formula

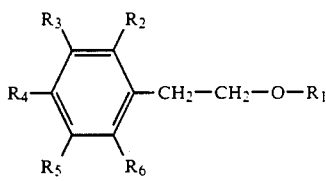

and the phenylglyoxal acetal is of the formula

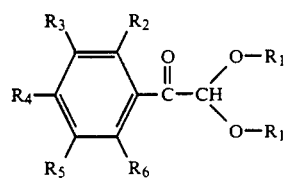

wherein $R_1$ is a primary or a secondary alkyl group and $R_2$, $R_3$, $R_4$, $R_5$ and $R_6$, are independently hydrogen, an alkyl group, an unsubstituted or a substituted aryl group, a hydroxy group, an alkoxy group, an unsubstituted or a substituted aryloxy group, a halogen, a carboxylic acid group, a carboxylic acid derivative group, an acyloxy group, an aroyloxy group, an amino group, an alkyl substituted amino group, a substituted or an unsubstituted aryl substituted amino group.

3. The method according to claim 1 wherein said metal catalyst is selected from the group consisting of Group VIII metals of the periodic table of the elements.

4. The method according to claim 1 wherein the reducing step is carried out for a sufficient time to effect the reduction.

5. The method according to claim 1 further including the step of first preparing the phenylglyoxal acetal.

6. The method according to claim 5 wherein the first preparing step includes the step of interacting a hydroxyaromatic methylketones with a primary or a secondary alkyl alcohol in the presence of a nitrosonium ion (NO+) source and a hydrogen (H+) ion source.

7. A method of preparing a phenethanol ether of the formula

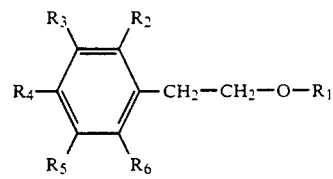

comprising the step of reacting a phenylglyoxal acetal of the formula

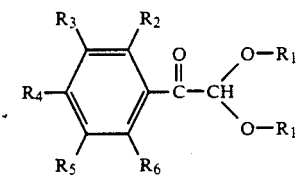

with hydrogen is the presence of a metal hydrogenation catalyst and a acid catalyst wherein $R_1$ is a primary or a secondary alkyl group and $R_2$, $R_3$, $R_4$, $R_5$ and $R_6$, are independently hydrogen, an alkyl group, an unsubstituted aryl group, a substituted aryl group, a hydroxy group, an alkoxy group, an unsubstituted or a substituted aryloxy group, a halogen, a carboxylic acid group, a carboxylic acid derivative group, an acyloxy group, an aroyloxy group, an amino group, an alkyl substituted amino group, a substituted or an unsubstituted aryl substituted amino group.

8. The method according to claim 7 wherein the acid catalyst is hydrogen chloride.

9. The method according to claim 7 wherein the metal catalyst is Pd, Pt or Ni.

10. The method according to claim 7 wherein $R_1$ is a methyl, an isopropyl or an isoamyl group, $R_4$ is hydroxy group, and $R_2$, $R_3$, $R_5$ and $R_6$ are hydrogen.

11. The method according to claim 7 wherein the reaction step is carried out at a temperature in the range of about $-20°$ C. to about $150°$ C.

12. The method according to claim 7 wherein the reaction step is carried out at hydrogen pressure in the range of about 15 psig to about 1000 psig.

* * * * *

UNITED STATES PATENT AND TRADEMARK OFFICE
CERTIFICATE OF CORRECTION

PATENT NO. : 5,124,489
DATED : June 23, 1992
INVENTOR(S) : John R. Durrwachter, et al It is certified that error appears in the above-indentified patent and that said Letters Patent is hereby corrected as shown below:

| | |
|---|---|
| Column 1, line 38 | Should read, "tion and Behavior of Spiro 2,5; octa-1,4-diene-3-one," |
| Column 7, line 15 | Should read, "cetals of the (formula 3)" |
| Column 7, line 41 | Should read, "stoichiometrically as follows. (Reaction 2)" |
| Column 7, line 60 | Delete, "at least a catalytic amount; preferably, how-" |
| Column 7, line 61 | Delete, "ever, it should be present in" |
| Column 7, line 62 | Should read, "amount of from about one (1) to about six (6) mole equiv-" |
| Column 9, line 38 | Should read, "tion mass by well known separation techniques such as" |
| Column 9, line 39 | Should read, "distillation, crystallization and filtration. For example" |
| Column 10, line 48 | Should read, "nuclear magnetic residence (nmr). [$^1$H-nmr (200 MHz," |
| Column 10, line 50 | Should read, "6.90, 8.0 (dd, 4 H, aromatic). 9.27 (s, 1 H, OH); $^{13}$C-nmr" |
| Column 11, line 8 | Should read, "catalyst being reacted with hydrogen gas pressurized at" |
| Column 11, line 51 | Should read, "nmr(200 MHz, acetone-d$_6$); $\delta$ 0.93 (m, 12 H, CH$_3$-), 1.4" |
| Column 11, line 53 | Should read, "(m, 4h, -OCH$_2$) 5.1 (s, 1H, O-CH-O), 6,9, 8.0" |

UNITED STATES PATENT AND TRADEMARK OFFICE
CERTIFICATE OF CORRECTION

PATENT NO. : 5,124,489
DATED : June 23, 1992
INVENTOR(S) : John R. Durrwachter, et al It is certified that error appears in the above-indentified patent and that said Letters Patent is hereby corrected as shown below:

| | |
|---|---|
| Column 12, line 8 | Should read, "4-Hydroxyphenylglyoxal Diisopropyl Acetal" |
| Column 12, line 29 | Should read, "spectroscopy and nmr. [$^1$H-nmr(200 MHz, acetone-$d_6$);" |
| Column 12, line 31 | Should read, "CH-(CH$_3$)$_2$, 5.14 (s, 1H, -CH -(O-iPr)$_2$), 6.89, 8.10" |
| Column 12, line 51 | Should read, "rated bicarbonate, dried over MgSO$_4$ and concentrated" |
| Column 14, line 22 | Should read, "catalyst and an acid catalyst wherein R$_1$ is a primary or a" |

Signed and Sealed this

Nineteenth Day of October, 1993

BRUCE LEHMAN

Attest:

Attesting Officer        Commissioner of Patents and Trademarks